US00PP20820P2

(12) United States Plant Patent
Kools

(10) Patent No.: US PP20,820 P2
(45) Date of Patent: Mar. 9, 2010

(54) ***METASEQUOIA GLYPTOSTROBOIDES* PLANT NAMED 'SHIRRMANN'S NORDLICHT'**

(50) Latin Name: *Metasequoia glyptostroboides*
Varietal Denomination: Shirrmann's Nordlicht

(76) Inventor: Cornelius Kools, Vlierdenseweg 115, Deurne (NL) 5753 AC ( * ) Notice: Subject to any disclaimer, the term of this patent is extended or adjusted under 35 U.S.C. 154(b) by 0 days.

(21) Appl. No.: 12/316,958

(22) Filed: Dec. 18, 2008

(51) Int. Cl.
*A01H 7/00* (2006.01)

(52) U.S. Cl. ..... Plt./213

(58) Field of Classification Search ..... Plt./213
See application file for complete search history.

*Primary Examiner*—Susan B McCormick Ewoldt
(74) *Attorney, Agent, or Firm*—Audrey Charles

(57) ABSTRACT

A new and distinct cultivar of *Metasequoia* plant named 'Shirrmann's Nordlicht', characterized by its medium green-colored leaves occasionally with greenish-white axial variegation, globe-shaped compact growth habit, and good garden performance, is disclosed.

2 Drawing Sheets

Latin name of genus and species of plant claimed: *Metasequoia glyptostroboides.*

Variety denomination: 'Shirrmann's Nordlicht'.

BACKGROUND OF THE INVENTION

The present invention relates to a new and distinct cultivar of *Metasequoia* plant botanically known as *Metasequoia glyptostroboides* and hereinafter referred to by the cultivar name 'Shirrmann's Nordlicht'.

The new *Metasequoia* cultivar is a naturally-occurring sport of 'White Spot', not patented, characterized by green leaves marked with subtle creamy-white variegation and a narrow, conical tree-like habit. The new cultivar was discovered as a branch sport and selected in 2004 in an outdoor nursery environment at Deurne, Germany.

Asexual reproduction of the new *Metasequoia* by grafting in a controlled environment in Deurne, Germany since 2006, has shown that the unique features of this new *Metasequoia* are stable and reproduced true to type in successive generations.

SUMMARY OF THE INVENTION

The following characteristics of the new cultivar have been repeatedly observed and can be used to distinguish 'Shirrmann's Nordlicht' as a new and distinct cultivar of *Metasequoia* plant:

1. Medium green-colored leaves occasionally with greenish-white axial variegation;
2. Globe-shaped compact growth habit; and
3. Good garden performance.

Of the many commercially available *Metasequoia* cultivars, the most similar in comparison to the new cultivar is the cultivar 'Mattheai', not patented. However, in comparison, plants of the new cultivar differ from 'Mattheai' in leaf color and plant habit. The new cultivar has variegated foliage and a more compact growth habit.

BRIEF DESCRIPTION OF THE PHOTOGRAPHS

The accompanying photographs show, as nearly true as it is reasonably possible to make the same in color illustrations of this type, typical foliage characteristics of the new cultivar. Colors in the photographs differ slightly from the color values cited in the detailed description, which accurately describes the colors of 'Shirrmann's Nordlicht'. The plants were grown outdoors in 2.5 liter containers for approximately 3 years in Deurne, The Netherlands.

FIG. 1 is a side perspective view of typical plants of 'Shirrmann's Nordlicht' grown in an outdoor nursery.

FIG. 1 is a close-up view of typical foliage of 'Shirrmann's Nordlicht'.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in August 2008 under natural light conditions in Deurne, The Netherlands when day temperatures ranged from 12° C. to 32° C. (53° F. to 90° F.) and night temperatures ranged from 6° C. to 18° C. (43° F. to 64° F.).

Plants used in the following description were grown in Deurne, The Netherlands, in an outdoor nursery in 3.5 liter containers and under conditions which closely approximate commercial production conditions. The plants were grown for approximately 3 years when the description was taken. Measurements and numerical values represent averages of typical plants.

Botanical classification: *Metasequoia glyptostroboides* cultivar Shirrmann's Nordlicht.

Parentage: Naturally-occurring branch sport of *Metasequoia glyptostroboides* 'White Spot', not patented.

Propagation:

*Type.*—Graft.

Plant description:

Growth habit and general appearance.—Globular, deciduous conifer perennial shrub having low to moderate vigor, growing an average of 10.0 cm per season.

*Crop time.*—Approximately 10 months from grafting to finish in an 11 cm container.

*Size.*—Plant height (from graft union): Approximately 25.0 cm. Plant width (spread): Approximately 29.4 cm.

*Trunk diameter.*—Midpoint above the soil line: approximately 1.6 cm. Texture: smooth. Color of trunk: 165A to 200D.

*Branches.*—Freely branching. Quantity: Approximately 27. Shape: Rounded. Appearance: Dull, covered with scale-like leaves, opposite in arrangement. Strength: Moderately strong. Length: Approximately 9.9 cm. Diameter: Approximately 2.0 mm. Internode length: Approximately 5.0 mm. Texture: Glabrous. Color of young stem: N170B to N170C. Color of mature stem: 175B to 175C.

Foliage description:

*General description.*—Type: Approximately 50% compound and 50% simple. Arrangement: Opposite. Quantity per lateral branch: Approximately 40. Texture of upper and lower surfaces: Smooth, glabrous. Venation pattern: Parallel. Color of upper surface of young foliage: 138B to 138C, slightly overlaid with N170B to N170C at the tips. Color of lower surface of young foliage: 138D. Color of upper surface of mature foliage: 138B occasionally with an axial variegation of 157A to 157B. Color of lower surface of mature foliage: 138D. Color of upper and lower surfaces of venation: Indistinguishable from leaf color.

*Leaves.*—Shape: Paripinnate, with an overall oblong shape. Appearance: Dull. Apex: Acute. Base: Attenuate. Margin: Entire. Length: Approximately 7.2 cm. Width: Approximately 1.7 cm. Leaflet shape: Ligulate. Leaflet apex: Acute. Leaflet base: Sessile. Leaflet margin: Entire. Leaflet length: Approximately 1.9 cm. Leaflet width: 1.8 mm.

*Petiole.*—Length: Approximately 5.0 mm. Diameter: Approximately 1.0 mm. Texture: Smooth, glabrous. Color: 138C.

Cone and seed production: Not available, cone and seed production have not been observed.

Disease and pest resistance: Plants of the new *Metasequoia* have not been noted to be resistant to pathogens and pests common to *Metasequoia.*

Weather tolerance: Plants of the new *Metasequoia* have been observed to be highly tolerant to rain and wind. Plants of the new *Metasequoia* have been observed to tolerate high temperatures of about 35° C. (95° F.) and to be hardy to a least USDA Zone 5.

What is claimed is:

1. A new and distinct cultivar of *Metasequoia* plant named 'Shirrmann's Nordlicht', substantially as herein shown and described.

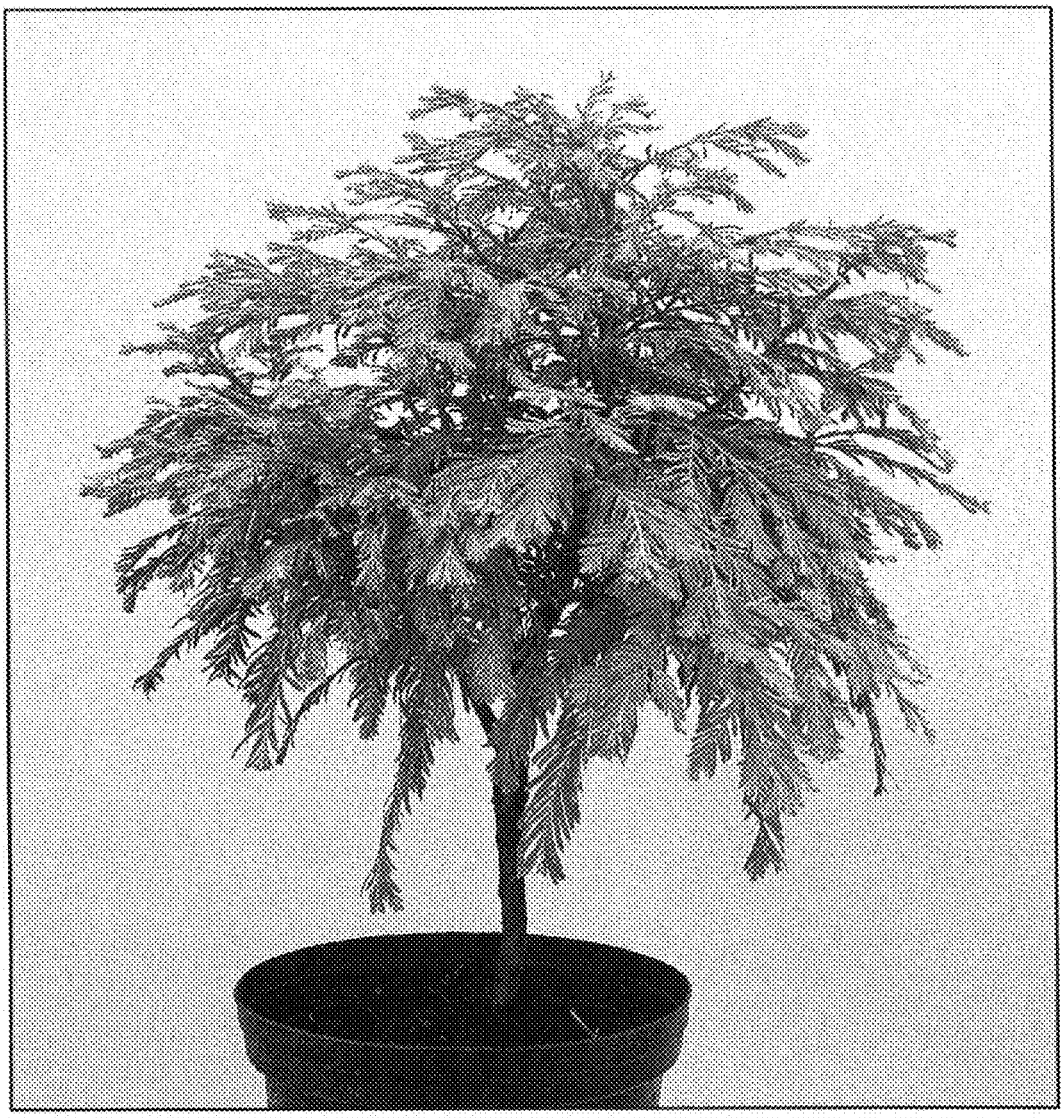

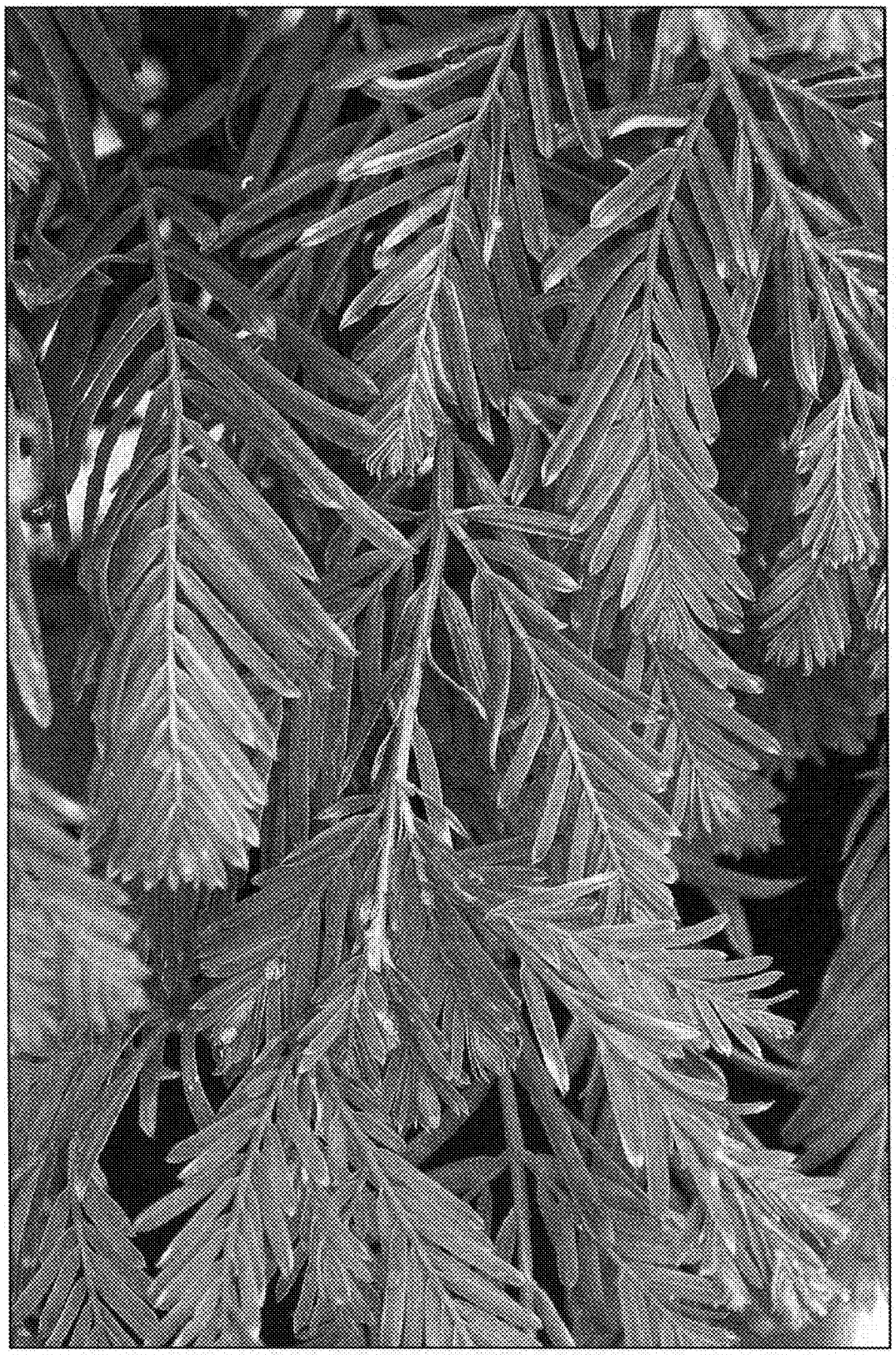

* * * * *